(12) United States Patent
Takemoto (10) Patent No.: US 10,099,010 B2
(45) Date of Patent: Oct. 16, 2018

(54) ASSEMBLY FOR SYRINGE, ASSEMBLY METHOD AND ASSEMBLY DEVICE FOR ASSEMBLING ASSEMBLY FOR SYRINGE, PRE-FILLED SYRINGE USING ASSEMBLY FOR SYRINGE, AND METHOD FOR ASSEMBLING PRE-FILLED SYRINGE

(71) Applicant: Terumo Kabushiki Kaisha, Tokyo (JP)

(72) Inventor: Masafumi Takemoto, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 497 days.

(21) Appl. No.: 14/640,980

(22) Filed: Mar. 6, 2015

(65) Prior Publication Data
US 2015/0174329 A1    Jun. 25, 2015

Related U.S. Application Data

(63) Continuation of application No. PCT/JP2013/057409, filed on Mar. 15, 2013.

(51) Int. Cl.
*A61M 5/32* (2006.01)
*A61M 5/28* (2006.01)
(Continued)

(52) U.S. Cl.
CPC .............. *A61M 5/28* (2013.01); *A61M 5/32* (2013.01); *A61M 5/3202* (2013.01); *B65B 3/003* (2013.01);
(Continued)

(58) Field of Classification Search
CPC ...... A61M 5/3202; A61M 5/343; A61M 5/28; A61M 5/34; A61M 5/32; A61M 5/3134; A61M 2005/3109; A61M 2207/00
(Continued)

(56) References Cited

U.S. PATENT DOCUMENTS 4,240,425 A * 12/1980 Akhavi ................. A61M 5/343
  604/192
4,342,184 A *  8/1982 Van Eck ................. A61J 1/067
  264/524
(Continued)

FOREIGN PATENT DOCUMENTS

JP    H08-206201 A    8/1996
JP    H08-508182 A    9/1996
(Continued)

OTHER PUBLICATIONS

International Search Report issued in International Patent Application No. PCT/JP2013/057409 dated May 28, 2013.
(Continued)

*Primary Examiner* — Laura Bouchelle
(74) *Attorney, Agent, or Firm* — Foley & Lardner LLP (57) ABSTRACT

A method for assembling an assembly for a syringe that includes a cylindrical outer barrel; a puncture needle; and a cylindrical cap. The method includes forming a closed space in a receiving hole of the cap by inserting the puncture needle and a barrel tip at least partially into the receiving hole before a tip end of the puncture needle is inserted into a bottom wall of the cap; discharging gas in the closed space; and sealing a tip end of the needle hole by further inserting the barrel tip into the receiving hole to insert the tip end of the puncture needle into the bottom wall.

10 Claims, 5 Drawing Sheets

(51) Int. Cl.
*B65B 3/00* (2006.01)
*B65B 55/10* (2006.01)
*A61M 5/31* (2006.01)

(52) U.S. Cl.
CPC ..... *B65B 55/10* (2013.01); *A61M 2005/3109* (2013.01); *A61M 2207/00* (2013.01); *Y10T 29/49826* (2015.01)

(58) Field of Classification Search
USPC ........ 604/192, 197, 199, 240, 243, 263, 264
See application file for complete search history.

(56) References Cited

U.S. PATENT DOCUMENTS

| | | | |
|---|---|---|---|
| 5,540,666 A | 7/1996 | Barta et al. | |
| 6,331,174 B1* | 12/2001 | Reinhard | A61M 5/28 427/2.3 |
| 6,629,963 B2* | 10/2003 | Prais | A61M 5/3202 206/365 |
| 7,468,055 B2* | 12/2008 | Prais | A61M 5/3202 604/272 |
| 2001/0039402 A1* | 11/2001 | Prais | A61M 5/3202 604/239 |
| 2001/0044608 A1* | 11/2001 | Odell | A61M 5/3202 604/199 |
| 2006/0079834 A1 | 4/2006 | Tennican et al. | |
| 2006/0247583 A1* | 11/2006 | Klint | A61M 5/329 604/264 |
| 2012/0010573 A1* | 1/2012 | Lundquist | A61M 5/3293 604/192 |
| 2013/0041241 A1 | 2/2013 | Felts et al. | |
| 2013/0174518 A1* | 7/2013 | Tachikawa | A61M 5/28 53/425 |

FOREIGN PATENT DOCUMENTS

| | | |
|---|---|---|
| JP | 2004-532060 A | 10/2004 |
| WO | WO 93/10422 A1 | 5/1993 |

OTHER PUBLICATIONS

Office Action issued in Chinese Patent Application No. 201380045960.3 dated Jan. 26, 2017.
Supplementary European Search Report issued in European Patent Application No. 13 878 107.5 dated Sep. 30, 2016.

* cited by examiner

ASSEMBLY FOR SYRINGE, ASSEMBLY METHOD AND ASSEMBLY DEVICE FOR ASSEMBLING ASSEMBLY FOR SYRINGE, PRE-FILLED SYRINGE USING ASSEMBLY FOR SYRINGE, AND METHOD FOR ASSEMBLING PRE-FILLED SYRINGE

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2013/057409 filed on Mar. 15, 2013, the entire contents of which is hereby incorporated by reference in its entirety.

BACKGROUND

Technical Field

The present disclosure relates to a syringe assembly including an outer barrel holding a puncture needle at its barrel tip, and a cap mounted detachably to the barrel tip; a method and an assembly device for assembling the syringe assembly; a pre-filled syringe using the syringe assembly; and a method for assembling the pre-filled syringe.

Background Art

As described in JP 2004-532060 W, in a pre-filled syringe preliminarily filled with a drug solution, a cap is mounted detachably to a barrel tip of an outer barrel provided with a puncture needle, for example. The cap mounted as described above protects the puncture needle, and seals a needle hole.

The cap is mounted before a plunger is inserted in a cylindrical space in the outer barrel or before a drug solution is filled in the outer barrel. A process of mounting the cap will specifically be described below.

A cap has a receiving hole for receiving a puncture needle. Firstly, a puncture needle is inserted into the receiving hole, and then, a barrel tip of an outer barrel is press-fitted to the receiving hole. In this case, an internal rib of the receiving hole is widened (elastically deformed) by the barrel tip inserted into the receiving hole. Therefore, the internal rib of the receiving hole tends to return to its original shape after the press-fit. With this, an inner wall surface of the receiving hole and a side face of the barrel tip of the outer barrel are in close contact with each other, whereby a closed space is formed between the receiving hole and the barrel tip of the outer barrel. At this point, a tip end of the puncture needle is not inserted into (does not reach) a bottom wall of the receiving hole. Therefore, the closed space is in communication with the atmosphere via the needle hole of the puncture needle and the inner space of the outer barrel. In other words, the closed space is not sealed.

The puncture needle and the barrel tip of the outer barrel are further inserted into the receiving hole, the tip end of the puncture needle is inserted into the bottom wall of the receiving hole, whereby the needle hole of the puncture needle is closed. Accordingly, the closed space is isolated from the atmosphere, and sealed.

The barrel tip of the outer barrel is then further inserted until the internal rib of the receiving hole is engaged with a portion where the outer diameter of the barrel tip of the outer barrel is reduced. As a result, the tip end of the puncture needle is further inserted into the bottom wall, and the cap is positioned to the barrel tip of the outer barrel due to an engagement between the internal rib of the receiving hole and the portion where the outer diameter of the barrel tip of the outer barrel is reduced, and friction resistance generated between the cap and the outer barrel.

As described above, the puncture needle and the barrel tip of the outer barrel are inserted into the receiving hole, and the cap is positioned to the barrel tip of the outer barrel, whereby the cap can be mounted detachably to the barrel tip of the outer barrel so as to seal the needle hole and the closed space. As a result, the puncture needle stored in the closed space can be protected from bacteria, and liquid (e.g., drug solution) can be filled between the inner space of the outer barrel and the plunger stored slidable in the inner space, in a liquid-tight manner. As described above, the process of mounting the cap to the barrel tip of the outer barrel includes a process of further inserting the barrel tip of the outer barrel into the receiving hole after the needle hole is closed to seal the closed space. In this case, gas remaining in the closed space with the sealed state is compressed by the barrel tip of the outer barrel inserted into the receiving hole. With this, the closed space has a positive pressure larger than the pressure around the cap (e.g., atmospheric pressure). Therefore, great force for further compressing the gas in the closed space against the positive pressure is needed to mount the cap to the barrel tip of the outer barrel.

Since the cap is mounted to the barrel tip of the outer barrel with the above positive pressure being generated, repulsive force is exerted between the cap and the barrel tip of the outer barrel in the direction in which the cap and the barrel tip are separated from each other. Due to this repulsive force, the cap is likely to be easily detached from the barrel tip of the outer barrel.

Especially when an assembly for a syringe is subject to a cleaning process, for example, the air around the assembly for a syringe is sucked for removing foreign materials, so that it is considered that the pressure around the cap is reduced and the positive pressure in the closed space is relatively increased. When an assembly for a syringe is sterilized with autoclave sterilization, or a sterilization method using sterilization gas such as ethylene oxide gas sterilization, or hydrogen peroxide gas sterilization, an inside of a sterilization device has to be depressurized before sterilization gas is supplied into the sterilization device having the assembly for a syringe inside. Therefore, pressure around the cap is reduced, and the positive pressure in the closed space is relatively increased. In the autoclave sterilization or ethylene oxide gas sterilization, the pressure in the sterilization device varies due to a volume fluctuation of gas caused by a temperature change, whereby it is considered that the positive pressure in the closed space becomes relatively larger than the pressure around the cap. When the positive pressure in the closed space becomes relatively larger than the pressure around the cap, the repulsive force increases to exceed friction resistance generated between the inner wall face of the receiving hole and the side face of the barrel tip of the outer barrel, resulting in that the cap might be detached more easily.

SUMMARY OF INVENTION

Certain embodiments of the present invention are accomplished in view of the above circumstance, and aim to provide an assembly for a syringe; a method and an assembly device for assembling the assembly for a syringe; a pre-filled syringe using the assembly for a syringe; and a method for assembling the pre-filled syringe, which can avoid a situation in which a closed space between a cap and a barrel tip of an outer barrel has an excessive positive pressure, can easily mount the cap to the barrel tip of the outer barrel, and can effectively prevent the mounted cap from being detached.

According to one embodiment, a method is provided for assembling an assembly for a syringe that includes a cylindrical outer barrel having a barrel tip at its tip end and an opening at its base end; a puncture needle held at the barrel tip and having a needle hole communicating with an inner space of the outer barrel; and a cylindrical cap having a receiving hole, which is formed in the direction in which the puncture needle extends and has a bottom wall at its tip end, the cap storing the puncture needle in the receiving hole and detachably mounted to the barrel tip so as to seal a tip end of the needle hole. The method includes a closed space forming process in which the puncture needle and the barrel tip are inserted into the receiving hole to form a closed space enclosed by the receiving hole and the barrel tip before the tip end of the puncture needle is inserted into the bottom wall; a gas discharge process of discharging gas in the closed space through the needle hole, the inner space, and the opening; and a sealing process of sealing the tip end of the needle hole by further inserting the barrel tip into the receiving hole to insert the tip end of the puncture needle into the bottom wall.

According to certain embodiments, upon inserting the puncture needle and the barrel tip into the receiving hole, gas within the closed space (receiving hole) is discharged through the needle hole and the inner space, before the tip end of the puncture needle reaches (is inserted into) the bottom wall to close the needle hole of the puncture needle. Due to such gas discharge, very little gas remains in the closed space, or even when gas remains, the gas has a reduced pressure compared to the pressure around the cap. Therefore, the generation of a positive pressure, which makes it difficult to further insert the barrel tip of the outer barrel into the receiving hole after the needle hole is closed to seal the closed space, in the closed space can be avoided. Accordingly, the cap can easily be mounted to the barrel tip of the outer barrel.

In addition, since the cap can be mounted to the barrel tip of the outer barrel with the generation of the positive pressure being avoided as described above, action of force (repulsive force) between the cap and the barrel tip of the outer barrel in the direction in which the cap and the barrel tip are separated from each other can be sufficiently suppressed or avoided.

From the above, the cap can easily be mounted to the barrel tip of the outer barrel, and the detachment of the cap mounted to the barrel tip of the outer barrel can effectively be prevented.

In one aspect, the gas is discharged such that the pressure in the closed space upon sealing the tip end of the needle hole in the sealing process becomes equal to or lower than an atmospheric pressure in the gas discharge process.

In this case, the cap can more easily be mounted to the barrel tip of the outer barrel, and the detachment of the cap mounted to the barrel tip of the outer barrel can more effectively be prevented.

In one aspect, the gas is discharged such that the pressure in the closed space upon sealing the tip end of the needle hole in the sealing process becomes equal to or lower than 80 kPa in the gas discharge process.

If the pressure in the closed space is equal to or lower than 80 kPa, the detachment of the cap mounted to the barrel tip of the outer barrel can surely be prevented, even when a pressure reduction process is performed to the assembly for a syringe, for example.

In one aspect, the gas is discharged such that the pressure in the closed space upon sealing the tip end of the needle hole in the sealing process becomes equal to or lower than 60 kPa in the gas discharge process.

If the pressure in the closed space is equal to or lower than 60 kPa, the detachment of the cap mounted to the barrel tip of the outer barrel can surely be prevented, even when autoclave sterilization is performed to the assembly for a syringe, for example.

In one aspect, the barrel tip includes an annular head portion, the receiving hole has a temporary stopper at a position where a length from the bottom wall is longer than a length from the tip end of the puncture needle to a tip end of the annular head portion, and the insertion of the puncture needle and the barrel tip into the receiving hole is temporarily stopped by allowing the tip end of the annular head portion to be in contact with the temporary stopper in the closed space forming process.

In this case, the insertion of the puncture needle and the barrel tip into the receiving hole can temporarily be stopped before the tip end of the puncture needle reaches the bottom wall of the receiving hole to close the needle hole of the puncture needle, whereby the closed space can easily and efficiently be formed in the closed space forming process.

In one aspect, the receiving hole has a small-diameter portion with a diameter smaller than an outer diameter of the annular head portion, and a large-diameter portion with a diameter larger than the annular head portion, the large-diameter portion being formed closer to the base end than the small-diameter portion, the temporary stopper is located between the small-diameter portion and the large-diameter portion, and the insertion of the puncture needle and the barrel tip into the receiving hole is temporarily stopped, and at the same time, the closed space is formed, by allowing the tip end of the annular head portion to be in contact with the temporary stopper in the closed space forming process.

In this case, the closed space can be formed simultaneous with the temporary stopper described above with a simple configuration in which the tip end of the annular head portion is brought into contact with the temporary stopper located between the small-diameter portion and the large-diameter portion. Therefore, the closed space can more easily and efficiently be formed in the closed space forming process.

In one aspect, the barrel tip has an annular head portion, the receiving hole has a stopper at a position where the length from the bottom wall is shorter than the length from the tip end of the puncture needle to the tip end of the annular head portion, and the insertion of the puncture needle and the barrel tip into the receiving hole is stopped by allowing the tip end of the annular head portion to be in contact with the stopper in the sealing process.

In this case, the further insertion of the barrel tip into the receiving hole can be prevented by allowing the tip end of the annular head portion to be in contact with the stopper. Therefore, the tip end of the puncture needle is not inserted to the bottom wall more than necessary. Accordingly, this configuration can more surely close the needle hole of the puncture needle, while preventing the tip end of the puncture needle from being damaged and preventing the tip end of the puncture needle from projecting from the cap.

Certain embodiments of the present invention include a process of supplying a drug solution from the opening into the inner space of the outer barrel of the assembly for a syringe assembled by the method of the described above and a process of sealing the side of the opening in the inner space by inserting a gasket into the inner space.

According to certain embodiments of the present invention, the above closed space forming process, the gas discharge process, and the sealing process are performed, whereby the cap is easily mounted to the barrel tip of the outer barrel to produce a pre-filled syringe. In this pre-filled syringe, the detachment of the cap mounted to the barrel tip of the outer barrel can effectively be prevented.

In one embodiment, an assembly device is provided for assembling an assembly for a syringe that includes a cylindrical outer barrel having a barrel tip at its tip end and an opening at its base end; a puncture needle held at the barrel tip and having a needle hole communicating with an inner space of the outer barrel; and a cylindrical cap having a receiving hole, which is formed in the direction in which the puncture needle extends and has a bottom wall at its tip end, the cap storing the puncture needle in the receiving hole and detachably mounted to the barrel tip so as to seal a tip end of the needle hole. The assembly device includes: a cap support unit that supports the cap; an outer barrel support unit that supports the outer barrel; a displacement unit that changes a relative position between the cap support unit and the outer barrel support unit so as to allow the puncture needle and the barrel tip to be inserted into the receiving hole; and a gas discharge unit that discharges gas through the needle hole, the inner space, and the opening. The displacement unit changes the relative position such that, after the barrel tip is inserted into the receiving hole, and a closed space enclosed by the receiving hole and the barrel tip is formed before the tip end of the puncture needle is inserted into the bottom wall of the receiving hole, the barrel tip is further inserted into the receiving hole and the tip end of the puncture needle is inserted into the bottom wall to seal the needle hole, and the gas discharge unit discharges gas in the closed space before the needle hole is closed by the insertion of the tip end of the puncture needle into the bottom wall.

This configuration can cause the closed space to have a pressure-reduced state by discharging gas in the closed space (receiving hole) by the gas discharge unit before the needle hole is closed, thereby facilitating the insertion of the barrel tip of the outer barrel into the receiving hole under the action of the displacement unit. This is because the generation of a positive pressure, which makes it difficult to mount the cap as described above, in the closed space can be avoided. Accordingly, the above method can easily be implemented.

In addition, the detachment of the cap mounted to the barrel tip of the outer barrel can effectively be prevented in the produced assembly for a syringe.

In one embodiment, an assembly for a syringe includes: a cylindrical outer barrel having a barrel tip at its tip end and an opening at its base end; a puncture needle held at the barrel tip and having a needle hole communicating with an inner space of the outer barrel; and a cylindrical cap having a receiving hole, which is formed in the direction in which the puncture needle extends and has a bottom wall at its tip end. The cap capable of storing the puncture needle in the receiving hole and being detachably mounted to the barrel tip so as to seal a tip end of the needle hole. A tip end of the puncture needle is inserted into the bottom wall so as to seal a tip end of the needle hole, and a pressure in the closed space enclosed by the receiving hole of the cap mounted to the barrel tip and the barrel tip is equal to or lower than an atmospheric pressure.

In the assembly for a syringe according to certain embodiments of the present invention, the cap is mounted to the barrel tip of the outer barrel in the state in which the generation of a positive pressure in the closed space is avoided. Therefore, action of repulsive force between the cap and the barrel tip of the outer barrel can sufficiently be suppressed or avoided. That is, the assembly for a syringe described above can effectively prevent the detachment of the cap mounted to the barrel tip of the outer barrel.

In one aspect, the pressure in the closed space is equal to or lower than 80 kPa.

In this case, the detachment of the cap mounted to the barrel tip of the outer barrel can surely be prevented, even when a pressure reduction process is performed to the assembly for a syringe, for example.

In one aspect, the pressure in the closed space is equal to or lower than 60 kPa.

In this case, the detachment of the cap mounted to the barrel tip of the outer barrel can surely be prevented, even when autoclave sterilization is performed to the assembly for a syringe, for example.

In one aspect, the barrel tip includes an annular head portion, the receiving hole has a temporary stopper at a position where a length from the bottom wall is longer than a length from the tip end of the puncture needle to a tip end of the annular head portion, and the temporary stopper temporarily stops the insertion of the puncture needle and the barrel tip into the receiving hole by allowing the tip end of the annular head portion to be in contact with the stopper before the tip end of the puncture needle is inserted into the bottom wall, upon mounting the cap to the barrel tip.

This configuration can easily allow the closed space to have a pressure equal to or lower than an atmospheric pressure via the needle hole and the inner space, before the puncture needle reaches the bottom wall to close the needle hole upon mounting the cap to the barrel tip.

In one aspect, the receiving hole has a small-diameter portion with a diameter smaller than an outer diameter of the annular head portion, and a large-diameter portion with a diameter larger than the annular head portion. The large-diameter portion being formed closer to the base end than the small-diameter portion. The temporary stopper is located between the small-diameter portion and the large-diameter portion, and the temporary stopper temporarily stops the insertion of the puncture needle and the barrel tip into the receiving hole, and at the same time, forms the closed space, by allowing the tip end of the annular head portion to be in contact with the stopper before the tip end of the puncture needle is inserted into the bottom wall, upon mounting the cap to the barrel tip.

With this, the insertion of the puncture needle and the barrel tip into the receiving hole can temporarily be stopped, and at the same time, the closed space can be formed, upon mounting the cap to the barrel tip. That is, this configuration can easily and efficiently allow the closed space to have a pressure equal to or lower than an atmospheric pressure via the needle hole and the inner space.

In one aspect, the barrel tip has an annular head portion, the receiving hole has a stopper at a position where the length from the bottom wall is shorter than the length from the tip end of the puncture needle to the tip end of the annular head portion, and the stopper stops the insertion of the puncture needle and the barrel tip into the receiving hole by allowing the tip end of the annular head portion to be in contact with the stopper with the tip end of the puncture needle being inserted into the bottom wall, upon mounting the cap to the barrel tip.

In this case, the further insertion of the barrel tip into the receiving hole can be prevented by allowing the tip end of the annular head portion to be in contact with the stopper, upon mounting the cap to the barrel tip. Therefore, the tip end of the puncture needle is not inserted to the bottom wall more than necessary. Accordingly, this configuration can more surely close the needle hole of the puncture needle, while preventing the tip end of the puncture needle from being damaged and preventing the tip end of the puncture needle from projecting from the cap.

In one embodiment, a pre-filled syringe includes: the assembly for a syringe as described above; a drug solution filled in the inner space; and a gasket inserted into the inner space that seals the opening side of the inner space.

The pre-filled syringe according to certain embodiments of the present invention can effectively prevent the detachment of the cap mounted to the barrel tip of the outer barrel as described above.

DETAILED DESCRIPTION

An embodiment of a method for assembling an assembly for a syringe according to the present invention will be described in detail with reference to the accompanying drawings in relation to an assembly device that performs the method.

An assembly device for assembling an assembly for a syringe according to certain embodiments of the present invention assembles an assembly for a syringe by detachably mounting a cap to a barrel tip of an outer barrel before a plunger is mounted to the outer barrel forming a syringe. Firstly, an assembly 10 for a syringe (see FIG. 4) will be described with reference to FIGS. 1 to 4.

Figure 1:
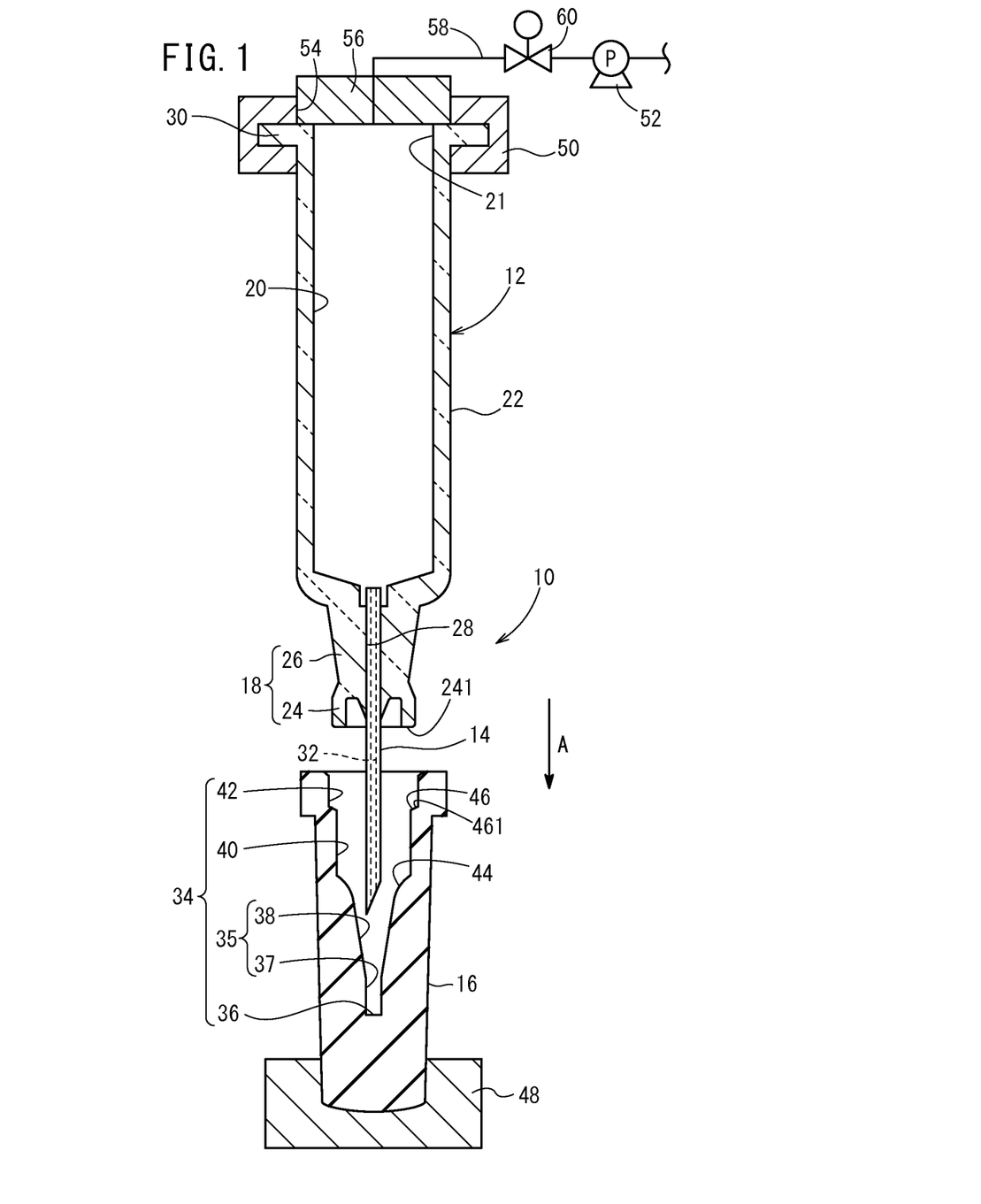
FIG. 1 is a schematic longitudinal sectional view illustrating a state in which a puncture needle and a barrel tip of an outer barrel are inserted into a receiving hole by an assembly device according to an embodiment of the present invention.

As illustrated in FIG. 1, the assembly 10 for a syringe includes an outer barrel 12, a puncture needle 14 held by the outer barrel 12, and a cap 16 covering the puncture needle 14.

The outer barrel 12 is a transparent or semi-transparent cylindrical member preferably made of a material having low oxygen permeability and low vapor permeability, such as polyester including polypropylene, polyethylene, polystyrene, polyamide, polycarbonate, polyvinyl chloride, poly-(4-methylpentene-1), acryl resin, acryl-nitrile-butadiene-styrene copolymer, or polyethylene terephthalate, various resins such as cyclic polyolefin, or a glass.

This outer barrel 12 has a barrel tip 18 holding the puncture needle 14, and an outer barrel body 22 at a base end of the barrel tip 18, the outer barrel body 22 having an inner space 20 and having a diameter larger than the barrel tip 18.

The outer barrel body 22 has an opening 21, which allows communication of the inner space 20 to the outside, at the base end.

The barrel tip 18 has an annular head portion 24 with generally a constant diameter in an axial direction of the outer barrel 12, and a columnar connection portion 26 that connects the annular head portion 24 and the outer barrel body 22, the connection portion 26 having a diameter temporarily reduced in a tapered shape from the annular head portion 24 and increased in a tapered shape toward the outer barrel body 22. The annular head portion 24 has a tip end surface 241, orthogonal to the extending direction (direction of an arrow A) of the puncture needle 14, at the annular head portion's tip end. The barrel tip 18 may have an extending portion (not illustrated) with a diameter smaller than the annular head portion at the tip end of the annular head portion 24.

A puncture needle support hole 28 communicating with the inner space 20 is formed from the annular head portion 24 to the outer barrel body 22. The puncture needle 14 is fixed to the puncture needle support hole 28, thereby being positioned and held at the barrel tip 18. Examples of the method of fixing the puncture needle 14 to the puncture needle support hole 28 include insert molding, heat welding with a high frequency or a laser, and bonding with an adhesive agent.

A flange 30 is formed integral with the outer barrel body 22 at the base end.

A needle hole 32 is formed to penetrate through the puncture needle 14 along the longitudinal direction of the puncture needle 14. This needle hole 32 is in communication with the inner space 20. When the cap 16 is mounted to the barrel tip 18, the tip end of the puncture needle 14 is inserted to a bottom wall 36 of a later-described receiving hole 34 of the cap 16, whereby the tip end of the needle hole 32 is sealed.

The cap 16 is a bottomed cylindrical body formed from an elastic body made of a rubber such as a butyl rubber, latex rubber, or silicon rubber; or a synthetic resin such as SBS elastomer, SEBS elastomer, or polyolefin elastomer. The cap 16 is detachably mounted to the barrel tip 18 of the outer barrel 12.

The cap 16 may be formed such that only the bottom wall 36 of the later-described receiving hole 34 is made of the above elastic body, and the other part may be made of a hard material harder than the above elastic body. Examples of the hard material include polypropylene, polyethylene, polystyrene, polyamide, polycarbonate, polyvinyl chloride, poly-(4-methylpentene-1), acryl resin, acryl-nitrile-butadiene-styrene copolymer, or polyethylene terephthalate, and various resins such as cyclic polyolefin.

The receiving hole 34 extending along the extending direction (direction of the arrow A) of the puncture needle 14 is formed in the cap 16. That is, an opening of the receiving hole 34 faces the barrel tip 18.

The receiving hole 34 has the bottom wall 36 formed at its tip end, a puncture needle storage portion 35 extending toward the base end from the bottom wall 36 to store the puncture needle 14, a small-diameter portion 40 that is formed closer to the base end than the puncture needle storage portion 35 and has an inner diameter generally constant, and a large-diameter portion 42 that is formed closer to the base end than the small-diameter portion 40 and has a diameter larger than the small-diameter portion 40. The puncture needle storage portion 35 has a deepest portion 37 slightly larger than the outer diameter of the puncture needle 14, and a tapered diameter-increasing portion 38 that extends from the deepest portion 37 with the diameter increasing toward the base end in a tapered form.

The inner diameter of the small-diameter portion 40 is larger than the inner diameter of the puncture needle storage portion 35, but slightly smaller than the outer diameter of the annular head portion 24. With this configuration, when the cap 16 is mounted to the barrel tip 18, the outer surface of the annular head portion 24 and the inner surface of the small-diameter portion 40 are in close contact with each other, whereby airtightness of a later-described closed space 62 enclosed by the receiving hole 34 and the barrel tip 18 is maintained.

The inner diameter of the large-diameter portion 42 is slightly larger than the outer diameter of the annular head portion 24 and the maximum diameter portion (base end of the barrel tip 18) of the connection portion 26. Due to this configuration, the annular head portion 24 can smoothly be inserted into the large-diameter portion 42. A curved stopper 44 is formed on the inner wall of the receiving hole 34 between the puncture needle storage portion 35 and the small-diameter portion 40, and a temporary stopper 46 is formed between the small-diameter portion 40 and the large-diameter portion 42.

The temporary stopper 46 has an annular temporary stopper surface 461 orthogonal to the extending direction (direction of the arrow A) of the puncture needle 14. Like the temporary stopper 46, the stopper 44 may also have an annular stopper surface orthogonal to the extending direction (direction of the arrow A) of the puncture needle 14.

Figure 2:
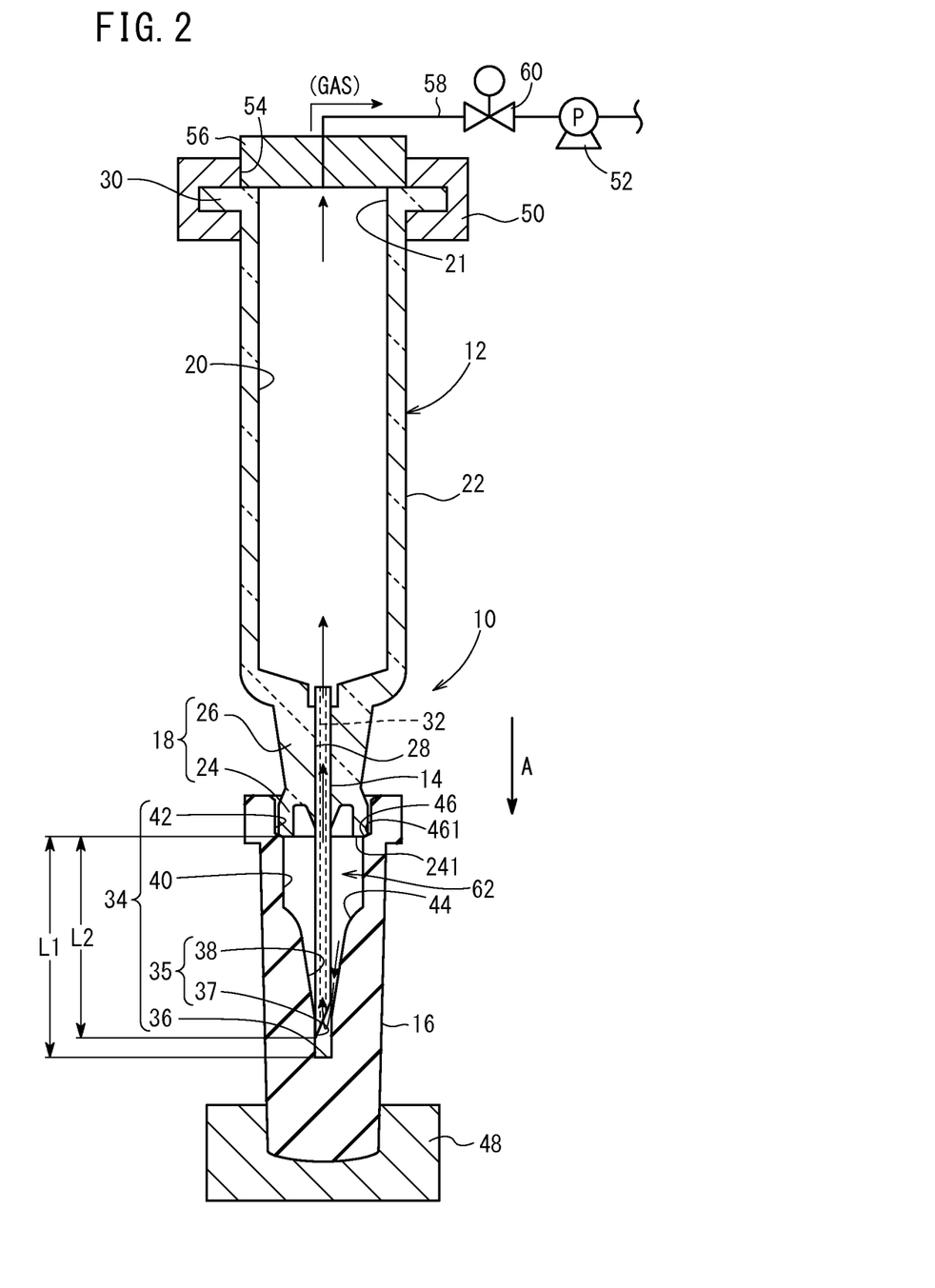
FIG. 2 is a schematic longitudinal sectional view illustrating a state in which gas in a closed space is discharged by the assembly device illustrated in FIG. 1.

As illustrated in FIG. 2, a length L1 from the bottom wall 36 of the receiving hole 34 to the temporary stopper 46 in the direction of the arrow A is set longer than a length L2 from the tip end of the puncture needle 14 to the tip end of the annular head portion 24 of the barrel tip 18. Therefore, when the tip end of the annular head portion 24 and the temporary stopper 46 are brought into contact with each other to form the closed space 62, the tip end of the puncture needle 14 is not inserted to the bottom wall 36, and hence, the tip end of the needle hole 32 is not sealed, as described later.

Figure 4:
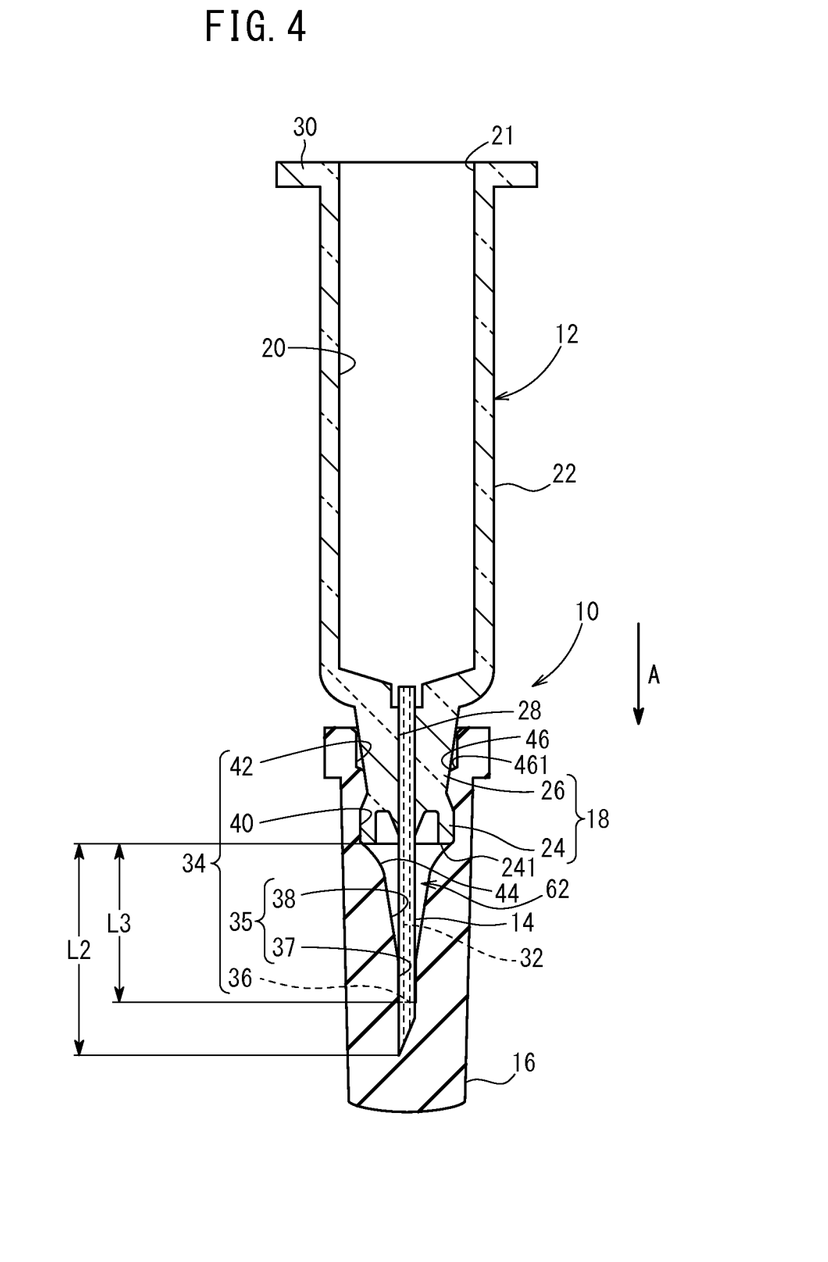
FIG. 4 is a schematic sectional view illustrating a state in which an assembly for a syringe is assembled by the assembly device illustrated in FIG. 1.

Also, as illustrated in FIG. 4, a length L3 from the bottom wall 36 of the receiving hole 34 to the stopper 44 in the direction of the arrow A is set shorter than the length L2 from the tip end of the puncture needle 14 to the tip end of the annular head portion 24 of the barrel tip 18. Therefore, when the tip end of the annular head portion 24 and the stopper 44 are brought into contact with each other to stop the insertion of the puncture needle 14 and the barrel tip 18 into the receiving hole 34, the tip end of the puncture needle 14 is inserted to the bottom wall 36, whereby the tip end of the needle hole 32 is sealed, as described later.

Figure 5:
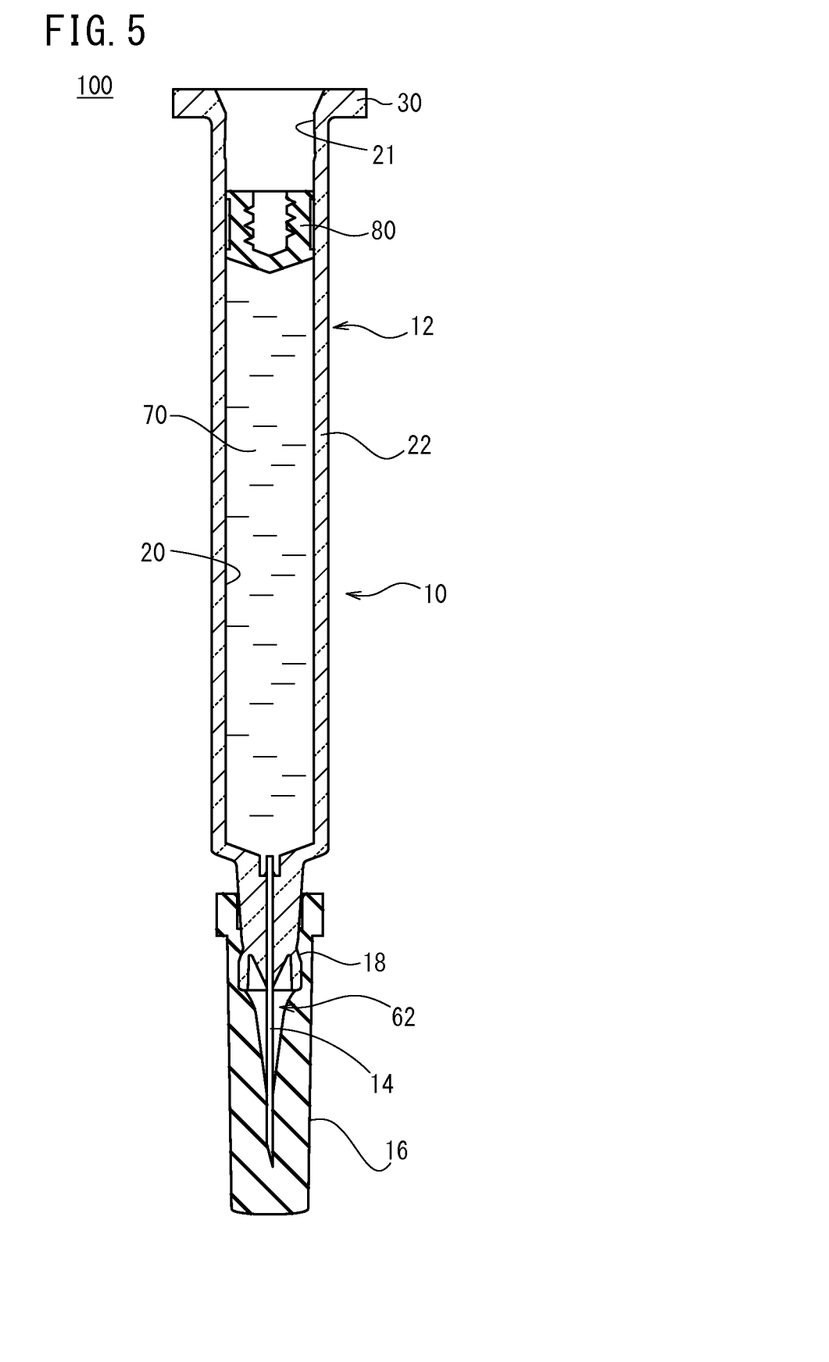
FIG. 5 is a schematic longitudinal sectional view illustrating a pre-filled syringe using the assembly for a syringe illustrated in FIG. 1.

As illustrated in FIG. 5, a pre-filled syringe 100 is composed of the above assembly 10 for a syringe, a drug solution 70 filled in the inner space 20, and a gasket 80 sealing the side of the opening 21 of the inner space 20. The pre-filled syringe 100 may include a plunger (not illustrated) mounted to the gasket 80. The assembly 10 for a syringe used for the pre-filled syringe 100 may undergo a cleaning process or a sterilization process, as necessary, before the drug solution 70 is filled in the inner space 20. The assembly 10 for a syringe may also undergo a sterilization process after being stored in a storage container for sterilization.

Next, a configuration of an assembly device according to an embodiment the present embodiment will be described.

Figure 3:
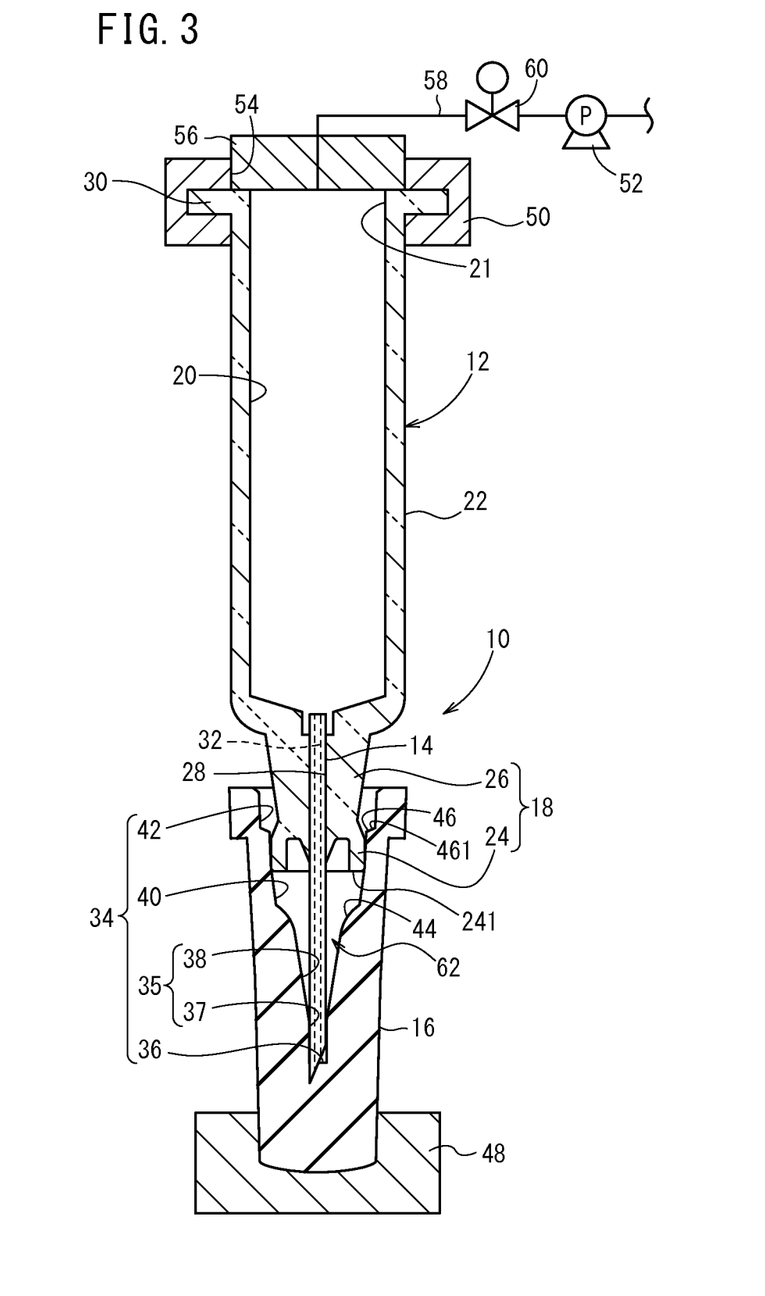
FIG. 3 is a schematic longitudinal sectional view illustrating a state in which a tip end of the puncture needle is inserted into a bottom wall of the receiving hole by the assembly device illustrated in FIG. 1.

As illustrated in FIGS. 1 to 3, the assembly device includes a first holder 48 serving as a cap supporting unit supporting the cap 16, a second holder 50 serving as an outer barrel holding unit holding the outer barrel 12, and a pump 52 serving as a gas discharge unit discharging gas in the receiving hole 34 via the needle hole 32 and the inner space 20.

In this case, the first holder 48 supports the vicinity of the bottom part of the cap 16, thereby holding the cap 16 in an upright position with its axis extending along a vertical direction. The second holder 50 is attached to the flange 30 to hold the outer barrel 12 at a position opposite to the cap 16 in an upright position with its axis extending along a vertical direction.

The first holder 48 and the second holder 50 can relatively be displaced along the direction of the arrow A under action of a displacement unit (not illustrated) mounted to a device body (not illustrated) of the assembly device, such as a fluid pressure cylinder or a servo cylinder. That is, the first holder 48 and the second holder 50 become close to each other or are separated from each other, and with such movement, the cap 16 and the outer barrel 12 become close to each other or are separated from each other. That is, the relative position between the cap 16 and the outer barrel 12 is changed.

Notably, only the first holder 48 (the cap 16) may be displaceable, or only the second holder 50 (the outer barrel 12) may be displaceable. It is obvious that both the first holder 48 (the cap 16) and the second holder 50 (the outer barrel 12) may be displaceable. The displacement unit may be a rack and pinion mechanism, for example.

An insertion hole 54 is formed to penetrate through the second holder 50 so as to communicate with the inner space 20 of the outer barrel 12. A closing member 56 is inserted into the insertion hole 54, whereby the opening 21 is closed. A seal is of course appropriately applied between the insertion hole 54 and the closing member 56.

A flexible exhaust pipe 58 connected to the pump 52 is mounted to the closing member 56. Therefore, when the pump 52 is activated, gas (e.g., air) in the inner space 20 and the receiving hole 34 is sucked by the pump 52 through the exhaust pipe 58. It is to be noted that a valve 60 is provided to the exhaust pipe 58 at the upstream side of the pump 52.

The assembly device according to the present embodiment is configured to include the above components, and its operation will be described next in relation to the assembly 10 for a syringe according to the present embodiment.

Firstly, as illustrated in FIG. 1, the first holder 48 supports the bottom part of the cap 16 to hold the cap 16 in an upright position with its axis extending along the vertical direction, and the second holder 50 supports the flange 30 of the outer barrel 12 to hold the outer barrel 12 at the position opposite to the cap 16 in an upright position with its axis extending along the vertical direction. The puncture needle 14 is fixed beforehand to the puncture needle support hole 28 formed at the barrel tip 18.

Next, after the closing member 56 is inserted into the insertion hole 54, at least one of the first holder 48 and the second holder 50 is displaced such that they are close to each other (in other words, the relative position is changed) by the unillustrated displacement unit (fluid pressure cylinder, for example). As a result, the puncture needle 14 and the barrel tip 18 of the outer barrel 12 are inserted into the receiving hole 34 of the cap 16 along the extending direction of the puncture needle 14 as illustrated in FIG. 2.

More specifically described, the annular head portion 24 of the barrel tip 18 is inserted into the large-diameter portion 42 of the receiving hole 34. Since the inner diameter of the large-diameter portion 42 is slightly larger than the outer diameter of the annular head portion 24, the annular head portion 24 can smoothly be inserted into the large-diameter portion 42. The annular head portion 24 is inserted to the large-diameter portion 42 until the tip end surface 241, that is the tip end of the annular head portion 24, is brought into contact with the temporary stopper 46. Thus, the closed space 62 enclosed by the receiving hole 34 and the barrel tip 18 (annular head portion 24) is formed.

Since the tip end surface 241, that is the tip end of the annular head portion 24, is brought into contact with the temporary stopper 46, the insertion of the puncture needle 14 and the barrel tip 18 into the receiving hole 34 is surely temporarily stopped, so that the insertion of the annular head portion 24 into the large-diameter portion 42 is ended. At this point, the tip end of the puncture needle 14 does not reach (is not inserted into) the bottom wall 36. Therefore, the needle hole 32 of the puncture needle 14 is not closed. Accordingly, the closed space 62 is in communication with the inner space 20 through the needle hole 32.

The contact between the tip end of the annular head portion 24 and the temporary stopper 46 is attained by the tip end surface 241 of the annular head portion 24 and the temporary stopper surface 461 of the temporary stopper 46. Since the tip end surface 241 of the annular head portion 24 and the temporary stopper surface 461 of the temporary stopper 46 are orthogonal to the extending direction of the puncture needle 14, i.e., the insertion direction of the barrel tip 18 into the receiving hole 34, the insertion of the puncture needle 14 and the barrel tip 18 into the receiving hole 34 is temporarily stopped with more certainty.

Next, until the tip end of the puncture needle 14 reaches the bottom wall 36 to close the needle hole 32, gas (generally, air) remaining in the closed space 62 is discharged. For this, the pump 52 may be activated, and the valve 60 may be opened. That is, gas remaining in the closed space 62 is sucked by the pump 52 via the needle hole 32, the inner space 20, and the opening 21, and further via the exhaust pipe 58. Due to this suction (gas discharge), the pressure in the closed space 62 becomes a negative pressure (equal to or lower than the atmospheric pressure).

The gas discharge by the pump 52 may be started before the closed space 62 is formed (e.g., from the state illustrated in FIG. 1), or after the closed space 62 is formed. In the former case, air is sucked through the needle hole 32 before the closed space 62 is formed.

As stated above, the barrel tip 18 is further inserted into the receiving hole 34 with the pressure in the closed space 62 being reduced to a negative pressure. That is, as illustrated in FIG. 3, the annular head portion 24 is inserted into the small-diameter portion 40, and the connection portion 26 is inserted into the large-diameter portion 42. It is to be noted that the temporary stopper 46 only stops the insertion of the annular head portion 24 at the tip end surface 241, and does not inhibit the annular head portion 24. Therefore, the temporary stopper 46 does not interrupt the insertion of the barrel tip 18.

Since the closed space 62 already has a negative pressure as described above, the compression of air to such an extent that the pressure in the closed space 62 becomes a positive pressure (atmospheric pressure) with the further insertion of the barrel tip 18 into the receiving hole 34 hardly occurs. Therefore, the tip end surface 241 of the annular head portion 24 does not receive large pressing force from the air in the closed space 62. Accordingly, the barrel tip 18 can easily be inserted into the receiving hole 34.

With such insertion, the tip end of the puncture needle 14 reaches the bottom wall 36, and is slightly inserted into the bottom wall 36. That is, the needle hole 32 is closed, resulting in that the closed space 62 is isolated from the needle hole 32 and the inner space 20. The discharge of the gas from the closed space 62 is ended by this isolation. When the valve 60 is closed with this state, the pressure in the closed space 62 is maintained to be a negative pressure. Thereafter, the pump 52 may be stopped. The gas discharge by the pump 52, i.e., the gas discharge from the closed space 62, may be ended before the needle hole 32 is closed (the state illustrated in FIG. 2, for example) after the closed space 62 is set to have a negative pressure.

The gas discharge amount by the pump 52 can be calculated from a change in a volume of the closed space 62 from the formation of the closed space 62 (see FIG. 2) till the tip end of the puncture needle 14 is inserted into the bottom wall 36 and stops at a predetermined position (see FIG. 4). More specifically, the gas discharge amount is adjusted such that the further insertion of the barrel tip 18 is not interrupted due to the generation of reaction force caused by the compression of air remaining in the closed space 62, i.e., the closed space 62 does not have an excessive positive pressure even if the air in the closed space 62 is compressed, when the barrel tip 18 is further inserted into the receiving hole 34.

Even after the needle hole 32 is closed, the insertion of the barrel tip 18 into the receiving hole 34 is continued. The insertion in this case is of course easy. This is because the closed space 62 has the negative pressure as described above. In this way, gas in the closed space 62 (receiving hole 34) is discharged by the pump 52 in the present embodiment. Therefore, the present embodiment prevents the closed space 62 from having a positive pressure due to the compression of air remaining in the closed space 62, or prevents the barrel tip 18 from receiving reaction force from the air due to the closed space 62 with the positive pressure, when the barrel tip 18 is further inserted into the receiving hole 34. Accordingly, the barrel tip 18 can easily be inserted into the receiving hole 34.

As a result of the insertion, the tip end of the puncture needle 14 is further inserted into the bottom wall 36, the tip end surface 241 that is the tip end of the annular head portion 24 is in contact with the stopper 44, and most of the connection portion 26 is inserted into the small-diameter portion 40 and the large-diameter portion 42, as illustrated in FIG. 4. The cap 16 is positioned to the barrel tip 18 of the outer barrel 12 by both the contact between the tip end surface 241 of the annular head portion 24 and the stopper 44 and friction resistance generated due to the close contact between the side wall of the annular head portion 24 and the inner wall of the small-diameter portion 40. As described above, the cap 16 is detachably mounted to the barrel tip 18 of the outer barrel 12.

Simultaneously, the opening of the cap 16 is closed by the barrel tip 18, whereby the closed space 62 is sealed with the negative pressure maintained. Due to the contact between the tip end surface 241 serving as the tip end of the annular head portion 24 and the stopper 44, the further insertion of the barrel tip 18 into the receiving hole 34 is prevented. Thus, the tip end of the puncture needle 14 is not inserted into the bottom wall 36 more than necessary, whereby damage on the tip end of the puncture needle 14 can be prevented, and the projection of the tip end of the puncture needle 14 from the cap 16 can also be prevented.

Next, the closing member 56 is removed from the insertion hole 54, and the first holder 48 and the second holder 50 are removed from the cap 16 and the outer barrel 12 respectively. Thus, the assembly 10 for a syringe having the cap 16 detachably mounted to the barrel tip 18 of the outer barrel 12 is released from the assembly device.

At this point, the inner space 20 is open to the atmosphere. However, the inside of the closed space 62 (receiving hole 34) keeps a negative pressure. This is because the needle hole 32 is closed as inserted into the bottom wall 36, and hence, the closed space 62 is isolated from the inner space 20.

That is, in this assembly 10 for a syringe, gas in the closed space 62 (receiving hole 34) is discharged to allow the closed space 62 to have a negative pressure (equal to or lower than the atmospheric pressure), and with this state, the cap 16 is mounted to the barrel tip 18, as described above. Therefore, this configuration can prevent the barrel tip 18 from being pressed by air in the closed space 62, and also prevent the generation of repulsive force between the cap 16 and the barrel tip 18. Accordingly, the detachment of the cap 16 mounted to the barrel tip 18 of the outer barrel 12 can effectively be prevented, even when a pressure reduction process for reducing a pressure is performed before foreign materials are sucked in a cleaning process or a sterilization process using sterilization gas, or when a sterilization process in which a temperature change occurs, such as autoclave sterilization or ethylene oxide gas sterilization, is performed to the assembly 10 for a syringe, for example.

Notably, the pressure in the closed space 62 (see FIG. 4) of the assembly 10 for a syringe is preferably equal to or lower than the atmospheric pressure, more preferably equal to or lower than 80 kPa, and most preferably equal to or lower than 60 kPa. If the pressure in the closed space 62 of the assembly 10 for a syringe is equal to or lower than 80 kPa, the detachment of the cap 16 mounted to the barrel tip 18 of the outer barrel 12 can surely be prevented, even when the pressure reduction process is performed to the assembly 10 for a syringe. If the pressure in the closed space 62 of the assembly 10 for a syringe is equal to or lower than 60 kPa, the detachment of the cap 16 mounted to the barrel tip 18 of the outer barrel 12 can surely be prevented, even when the autoclave sterilization is performed to the assembly 10 for a syringe.

As described above, according to the present embodiment, the cap 16 can easily be mounted to the barrel tip 18, whereby the assembly 10 for a syringe can easily be assembled. In addition, the detachment of the cap 16 can effectively be prevented in the assembly 10 for a syringe thus obtained.

The drug solution 70 is supplied to the assembly 10 for a syringe in the inner space 20 of the outer barrel 12 from the opening 21, and the opening 21 of the inner space 20 is closed by inserting the gasket 80 into the inner space 20, whereby the pre-filled syringe 100 is produced. In this case, the needle hole 32 and the closed space 62 are sufficiently sealed in the assembly 10 for a syringe. Therefore, the puncture needle 14 stored in the closed space 62 can be protected from bacteria, and further, the liquid drug solution 70 can be filled between the inner space 20 and the gasket 80 slidably inserted into the inner space 20.

While the present invention has been described above with reference to the exemplary embodiment, the invention is not limited to the disclosed exemplary embodiment, and it is obvious that various modifications are possible without departing from the scope of the present invention.

For example, the pre-filled syringe 100 is produced in the above embodiment. However, the assembly 10 for a syringe is not particularly limited to produce a pre-filled syringe, and other syringes can be produced.

The gas discharge in the closed space 62 is not necessarily performed until the inside of the closed space 62 becomes a negative pressure. For example, the gas discharge may be stopped at the point at which the pressure in the closed space 62 becomes almost equal to the external pressure (atmospheric pressure). If the detachment of the cap 16 mounted to the barrel tip 18 can be avoided, the pressure may be somewhat positive.

In addition, the outer barrel 12 and the cap 16 may be held in a horizontal position such that they are arranged along a horizontal direction, and with this state, the relative position between them may be changed to mount the cap 16 to the barrel tip 18 of the outer barrel 12.

In the above embodiment, the assembly device has the closing member 56 that closes the opening 21 of the outer barrel 12. However, gas in the closed space 62 may be sucked (discharged) together with ambient air around the outer barrel 12 without providing the closing member 56. In this case, the exhaust pipe 58 may be inserted into the inner space 20 to make it easy to suck the air in the closed space 62. Even in this case, the gas in the closed space 62 is sucked through the inner space 20 and the exhaust pipe 58 inserted into the opening 21, whereby the gas in the closed space 62 is discharged through the needle hole 32, the inner space 20, and the opening 21.

In the above embodiment, the closed space 62 is set to have a negative pressure (equal to or lower than the atmospheric pressure) by discharging gas in the closed space 62 enclosed by the receiving hole 34 of the cap 16 and the barrel tip 18 of the outer barrel 12. However, the closed space 62 may have a negative pressure (equal to or lower than the atmospheric pressure) by mounting the cap 16 to the barrel tip 18 of the outer barrel 12 in a pressure-reduced chamber having a negative pressure.

What is claimed is:

1. A method for assembling an assembly for use in a syringe, the assembly comprising a cylindrical outer barrel having a barrel tip at its tip end and an opening at its base end; a puncture needle held at the barrel tip and having a needle hole communicating with an inner space of the outer barrel; and a cylindrical cap having a receiving hole, which is formed in the direction in which the puncture needle extends and has a bottom wall at its tip end, the cap storing the puncture needle in the receiving hole and being detachably mounted to the barrel tip so as to seal a tip end of the needle hole, the method comprising:
   forming a closed space in the receiving hole by inserting the puncture needle and the barrel tip at least partially into the receiving hole before a tip end of the puncture needle is inserted into the bottom wall;
   discharging gas from the closed space through a discharging path defined by the needle hole of the puncture needle, the inner space of the barrel, and the opening of the barrel; and
   after or while discharging the gas from the closed space through the discharging path, further inserting the barrel tip into the receiving hole so as to seal the end of the needle hole by inserting the tip end of the puncture needle into the bottom wall.

2. The method according to claim 1, wherein the gas is discharged such that the pressure in the closed space upon sealing the tip end of the needle hole in the sealing step becomes equal to or less than an atmospheric pressure.

3. The method according to claim 1, wherein the gas is discharged such that the pressure in the closed space upon sealing the tip end of the needle hole in the sealing step becomes equal to or less than 80 kPa.

4. The method according to claim 1, wherein the gas is discharged such that the pressure in the closed space upon sealing the tip end of the needle hole in the sealing step becomes equal to or less than 60 kPa.

5. The method according to claim 1,
wherein the barrel tip includes an annular head portion,
wherein the receiving hole includes a temporary stopper at a position such that a length from the bottom wall to the temporary stopper is longer than a length from the tip end of the puncture needle to a tip end of the annular head portion, and
wherein the insertion of the puncture needle and the barrel tip into the receiving hole is temporarily stopped by the tip end of the annular head portion coming into contact with the temporary stopper during the step of forming the closed space.

6. The method according to claim 5,
wherein the receiving hole includes a small-diameter portion with a diameter smaller than an outer diameter of the annular head portion, and a large-diameter portion with a diameter larger than the annular head portion, the large-diameter portion being formed closer to the base end than the small-diameter portion, and
wherein the temporary stopper is located between the small-diameter portion and the large-diameter portion.

7. The method according to claim 1,
wherein the barrel tip includes an annular head portion,
wherein the receiving hole includes a stopper at a position such that a length from the bottom wall to the stopper is shorter than a length from the tip end of the puncture needle to the tip end of the annular head portion, and
wherein the insertion of the puncture needle and the barrel tip into the receiving hole is stopped by the tip end of the annular head portion coming into contact with the stopper during the sealing step.

8. The method according to claim 5,
wherein the receiving hole includes an additional stopper at a position such that a length from the bottom wall to the additional stopper is shorter than the length from the tip end of the puncture needle to the tip end of the annular head portion, and
wherein the insertion of the puncture needle and the barrel tip into the receiving hole is stopped by the tip end of the annular head portion coming into contact with the additional stopper during the sealing step.

9. The method according to claim 1, further comprising:
supplying a drug solution from the opening into the inner space of the outer barrel, and
inserting a gasket into the inner space.

10. A method for assembling an assembly for use in a syringe, the assembly comprising a cylindrical outer barrel having a barrel tip at its tip end and an opening at its base end; a puncture needle held at the barrel tip and having a needle hole communicating with an inner space of the outer barrel; and a cylindrical cap having a receiving hole, which is formed in the direction in which the puncture needle extends and has a bottom wall at its tip end, the cap storing the puncture needle in the receiving hole and being detachably mounted to the barrel tip so as to seal a tip end of the needle hole, the method comprising:
forming a closed space in the receiving hole by inserting the puncture needle and the barrel tip at least partially into the receiving hole before a tip end of the puncture needle is inserted into the bottom wall;
discharging gas from the closed space through the needle hole, the inner space, and the opening; and
sealing the tip end of the needle hole by further inserting the barrel tip into the receiving hole to insert the tip end of the puncture needle into the bottom wall;
wherein the barrel tip includes an annular head portion,
wherein the receiving hole includes a temporary stopper at a position such that a length from the bottom wall to the temporary stopper is longer than a length from the tip end of the puncture needle to a tip end of the annular head portion,
wherein the insertion of the puncture needle and the barrel tip into the receiving hole is temporarily stopped by the tip end of the annular head portion coming into contact with the temporary stopper during the step of forming the closed space,
wherein the receiving hole includes an additional stopper at a position such that a length from the bottom wall to the additional stopper is shorter than the length from the tip end of the puncture needle to the tip end of the annular head portion, and
wherein the insertion of the puncture needle and the barrel tip into the receiving hole is stopped by the tip end of the annular head portion coming into contact with the additional stopper during the sealing step.

* * * * *